(12) United States Patent
Ozawa

(10) Patent No.: US 11,986,406 B2
(45) Date of Patent: May 21, 2024

(54) STENT

(71) Applicant: OLYMPUS CORPORATION, Tokyo (JP)

(72) Inventor: Kosuke Ozawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 163 days.

(21) Appl. No.: 17/591,686

(22) Filed: Feb. 3, 2022

(65) Prior Publication Data
US 2022/0257393 A1 Aug. 18, 2022

Related U.S. Application Data

(60) Provisional application No. 63/149,686, filed on Feb. 16, 2021.

(51) Int. Cl.
*A61F 2/90* (2013.01)

(52) U.S. Cl.
CPC ........ *A61F 2/90* (2013.01); *A61F 2220/0075* (2013.01); *A61F 2250/001* (2013.01)

(58) Field of Classification Search
CPC ....... A61F 2/90; A61F 2/89; A61F 2220/0075
See application file for complete search history.

(56) References Cited

U.S. PATENT DOCUMENTS

| | | | | |
|---|---|---|---|---|
| 5,938,697 A | * | 8/1999 | Killion | A61F 2/915 623/1.15 |
| 6,159,238 A | * | 12/2000 | Killion | A61F 2/91 623/1.11 |
| 6,258,117 B1 | * | 7/2001 | Camrud | A61F 2/90 623/1.16 |
| 6,355,057 B1 | * | 3/2002 | DeMarais | A61F 2/91 623/1.15 |
| 8,313,522 B2 | | 11/2012 | Shin et al. | |
| 9,585,779 B2 | * | 3/2017 | Papp | B29C 65/64 |
| 10,251,763 B2 | * | 4/2019 | Wang | A61F 2/86 |
| 11,013,623 B2 | * | 5/2021 | Han | A61F 2/07 |
| 11,497,636 B2 | * | 11/2022 | Xiao | A61F 2/89 |
| 11,590,315 B2 | * | 2/2023 | Miura | A61L 29/06 |

(Continued)

FOREIGN PATENT DOCUMENTS

| | | |
|---|---|---|
| JP | 4451421 B2 | 4/2010 |
| WO | 2000/028923 A1 | 5/2000 |

(Continued)

OTHER PUBLICATIONS

Office Action dated Jan. 24, 2023, issued in corresponding Japanese Patent Application No. 2022-016608.

*Primary Examiner* — Suzette J Gherbi
(74) *Attorney, Agent, or Firm* — Morgan, Lewis & Bockius LLP

(57) ABSTRACT

A stent comprises a wire that is woven into a tubular fence forming a stent body, a plurality of tubular units connected around a longitudinal center axis of the stent body, and a plurality of connecting locations configured to connect adjacent ones of the plurality of tubular units and arranged along a plurality of circumferences with respect to the longitudinal center axis of the stent body. The plurality of circumferences include a first circumference having a first radius and a second circumference having a second radius, and the first radius is different from the second radius in length.

18 Claims, 11 Drawing Sheets

(56) References Cited

U.S. PATENT DOCUMENTS

| | | | | |
|---|---|---|---|---|
| 2001/0004705 A1* | 6/2001 | Killion | ............... | A61F 2/91 |
| | | | | 623/1.2 |
| 2001/0047199 A1* | 11/2001 | Wijay | ............... | A61F 2/91 |
| | | | | 623/1.15 |
| 2002/0095208 A1* | 7/2002 | Gregorich | ............ | A61F 2/915 |
| | | | | 623/1.15 |
| 2002/0116049 A1* | 8/2002 | Girton | ............... | A61F 2/91 |
| | | | | 623/1.15 |
| 2004/0254630 A1* | 12/2004 | Yang | ............... | A61F 2/915 |
| | | | | 623/1.15 |
| 2007/0173927 A1 | 7/2007 | Shin et al. | | |
| 2007/0213810 A1* | 9/2007 | Newhauser | ............ | A61F 2/91 |
| | | | | 623/1.16 |
| 2008/0221664 A1* | 9/2008 | Bales | ............... | A61F 2/88 |
| | | | | 623/1.22 |
| 2020/0138609 A1* | 5/2020 | Rangwala | ............. | A61F 2/95 |
| 2023/0277184 A1* | 9/2023 | Rashidi | ......... | A61B 17/12113 |
| | | | | 606/200 |
| 2023/0277723 A1* | 9/2023 | Roth | ............... | A61L 27/507 |
| | | | | 623/1.15 |

FOREIGN PATENT DOCUMENTS

| | | | |
|---|---|---|---|
| WO | 2012/120953 | A1 | 9/2012 |
| WO | 2020/049734 | A1 | 3/2020 |
| WO | 2020/050292 | A1 | 3/2020 |
| WO | 2020/054027 | A1 | 3/2020 |
| WO | 2020/194506 | A1 | 10/2020 |

\* cited by examiner

2nd line   1st line

Cross-section of stent when expanded

Cross-section of stent during storage into a delivery device

| | Expanding force @φ4 [N] | Anti-reducing force @φ4 [N] | Reducing reducing force @φ2.3 [N] |
|---|---|---|---|
| No radial offset | 14.4 | 28.2 | 89.8 |
| With radial offset | 15.3 | 26.1 | 54.8 |
| Difference | 1.0 | -2.1 | -35.1 |
| Difference[%] | 7% | -8% | -39% |

STENT

RELATED APPLICATION DATA

This application is based on and claims priority under 35 U.S.C. § 119 to U.S. Provisional Application No. 63/149,686, filed Feb. 16, 2021, the entire contents of which are incorporated herein by reference.

FILED OF THE INVENTION

The present invention relates to a stent, and more particularly, to a self-expandable stent.

DESCRIPTION OF THE RELATED ART

In recent years, stent placement has been used to expand and hold a lumen of a tubular organ by placing a stent made of wires or the like in an affected area where stenosis or occlusion has occurred in the lumen of the tubular organ in a patient.

Typically, a stent will have an unexpanded (reduced or closed) diameter for placement and an expanded (opened) diameter after placement in the vessel or the duct. Some stents are self-expanding; some stents are expanded mechanically with radial outward force from within the stent, as by inflation of a balloon; and some stents, known as hybrid stents, have one or more characteristics common to both self-expanding and mechanically expandable stents.

FIG. 1A is a perspective side view schematically illustrating part of a conventional self-expanded stent, which is formed by weaving wires into a cylindrically shaped stent. The conventional stent includes a plurality of tubular units connected by a plurality of connecting portions arranged along circumferential lines defined by the cylindrical shape of the stent. For explanation purpose, FIG. 1A only shows two of such tubular units which are connected at a plurality of connecting locations (A1-A5 shown in FIG. 1A). FIG. 1B is a front view (or cross-sectional view) schematically illustrating the tubular unit of 1st line in FIG. 1A and showing a plurality of circumferential sections 1-11. As shown in FIG. 1B, the plurality of circumferential sections 1-11 are arranged along one circumferential line (1st line in FIG. 1A) of the stent. While not labeled in FIG. 1B, there are also a plurality of connecting locations and a plurality of circumferential sections arranged along another one circumferential line (2nd line in FIG. 1A).

FIGS. 2A and 2B are front views (or cross-sectional views) schematically showing the conventional stent when it is in a delivery configuration. Since the stent has to be delivered via an inner sheath 50 in an unexpanded diameter state (reduced in diameter state) and covered by an outer sheath 60 to a desired bodily location. Once at the desired bodily location, the outer sheath 60 is pulled back to expose the stent so that the stent can be expanded and implanted in the bodily lumen. As shown in FIGS. 2A and 2B, when the conventional stent is reduced in diameter to be stored between the inner sheath 50 and the outer sheath 60, an external force is required to deform the wires by pushing the adjacent ones of the circumferential sections 1-11 of the wires against each other. As a result, the stent is stored disorderly or cannot be stored uniformly such that the space between the inner sheath 50 and the outer sheath 60 becomes sparse and dense depending on the locations of the connecting locations, which cause an increase in radial thickness because of the disorderly overlapping wires at the connecting locations. This situation also causes difficulty to recapture the stent in the body.

SUMMARY OF THE INVENTION

Accordingly, the present disclosure is directed to a stent, which substantially obviates one or more of the issues due to limitations and disadvantages of related stent delivery device and system.

An object of the present disclosure is to provide a stent comprises a wire that is woven into a tubular fence forming a stent body, a plurality of tubular units connected around a longitudinal center axis of the stent body, and a plurality of connecting locations configured to connect adjacent ones of the plurality of tubular units and arranged along a plurality of circumferences with respect to the longitudinal center axis of the stent body. The plurality of circumferences include a first circumference having a first radius and a second circumference having a second radius, and the first radius is different from the second radius in length.

Another object of the present disclosure is to provide a stent comprises a wire that is woven into a tubular fence, a first entangled connecting portion that is formed by hooking a first bent portion and a second bent portion of the wire, and a second entangled connecting portion that is formed by hooking a third bent portion and a fourth bent portion of the wire. The first bent portion is adjacent to the third bent portion along a circumferential direction, and the second bent portion is adjacent to the fourth bent portion along the circumferential direction. A first radial distance between the first entangled connecting portion and a longitudinal center axis of the stent is different from a second radial distance between the second entangled connecting portion and the longitudinal center axis of the stent.

Additional features and advantages will be set forth in the description that follows, and in part will be apparent from the description, or may be learned by practice of the invention. The objectives and other advantages of the disclosed stents and stent delivery device and system will be realized and attained by the structure particularly pointed out in the written description and claims thereof as well as the appended drawings.

BRIEF DESCRIPTION OF THE DRAWINGS

The following detailed description of preferred embodiments can be read in connection with the accompanying drawings in which like numerals designate like elements and in which.

Figure 1A:
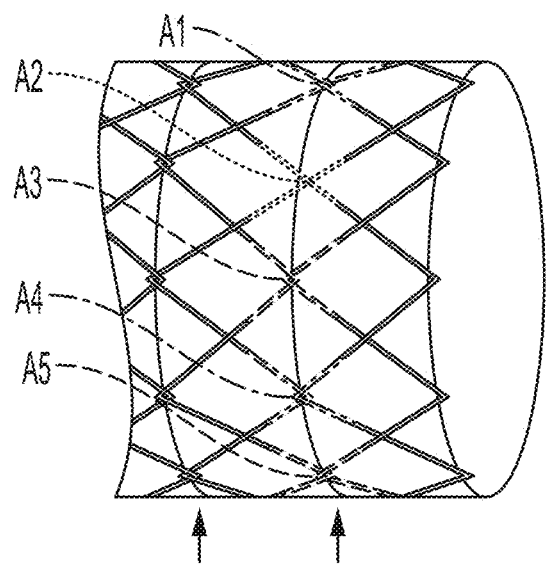
FIG. 1A is a perspective view schematically showing part of a conventional self-expanded stent.
Figure 1B:
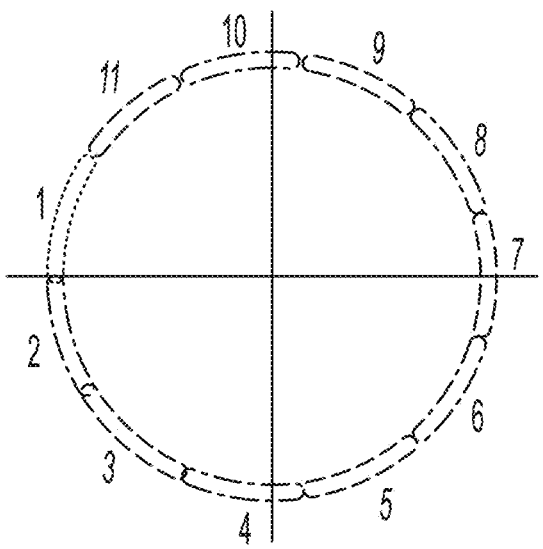
FIG. 1B is a front view (or cross-sectional view) of FIG. 1A.
Figure 2A:
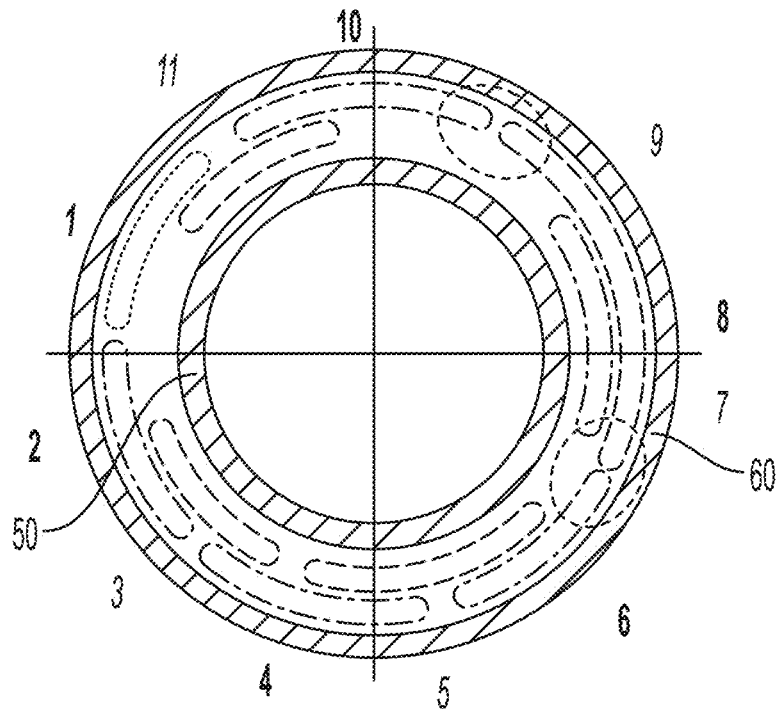
FIGS. 2A and 2B are cross-sectional views schematically showing the conventional stent of FIG. 1A when it is in a delivery configuration.
Figure 2B:
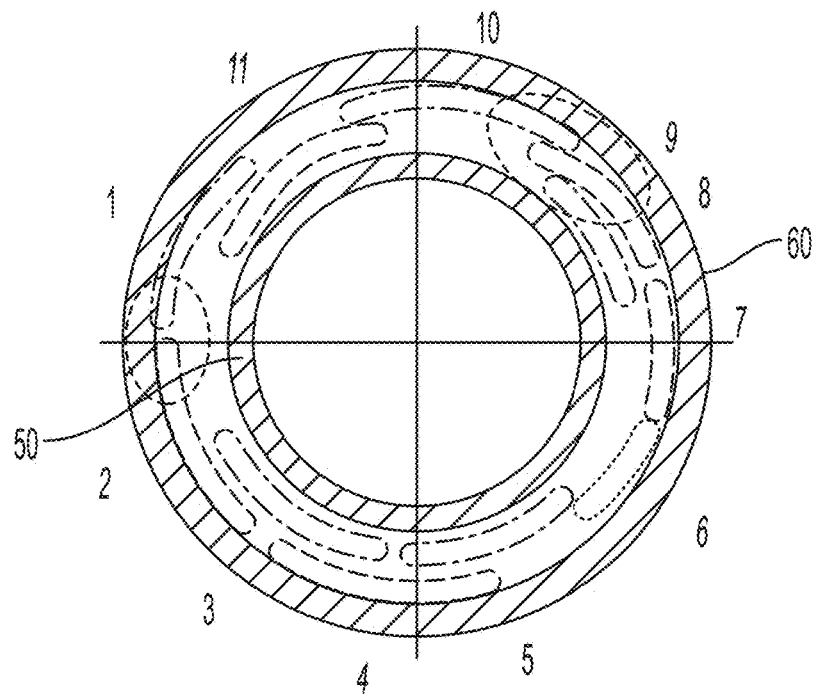

Throughout all of the drawings, dimensions of respective constituent elements are appropriately adjusted for clarity. For ease of viewing, in some instances only some of the named features in the figures are labeled with reference numerals.

DETAILED DESCRIPTION

Figure 3:
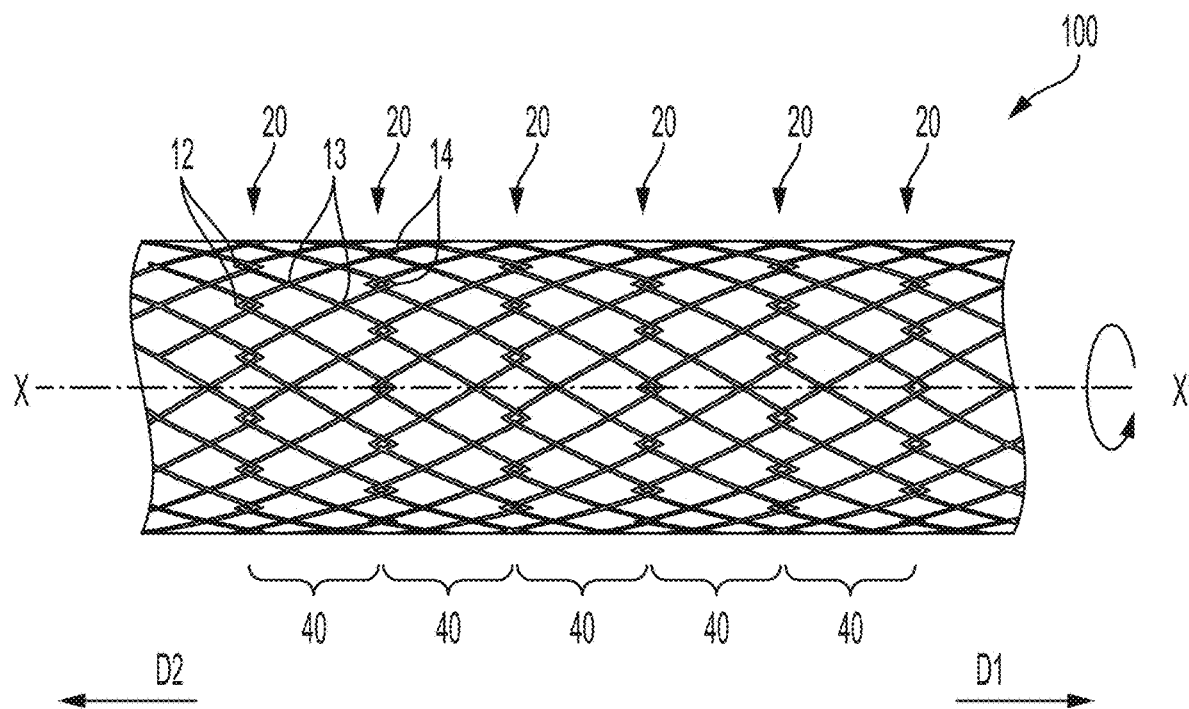
FIG. 3 is a diagram schematically showing an overall configuration of a stent according to an exemplary embodiment.
Figure 4:
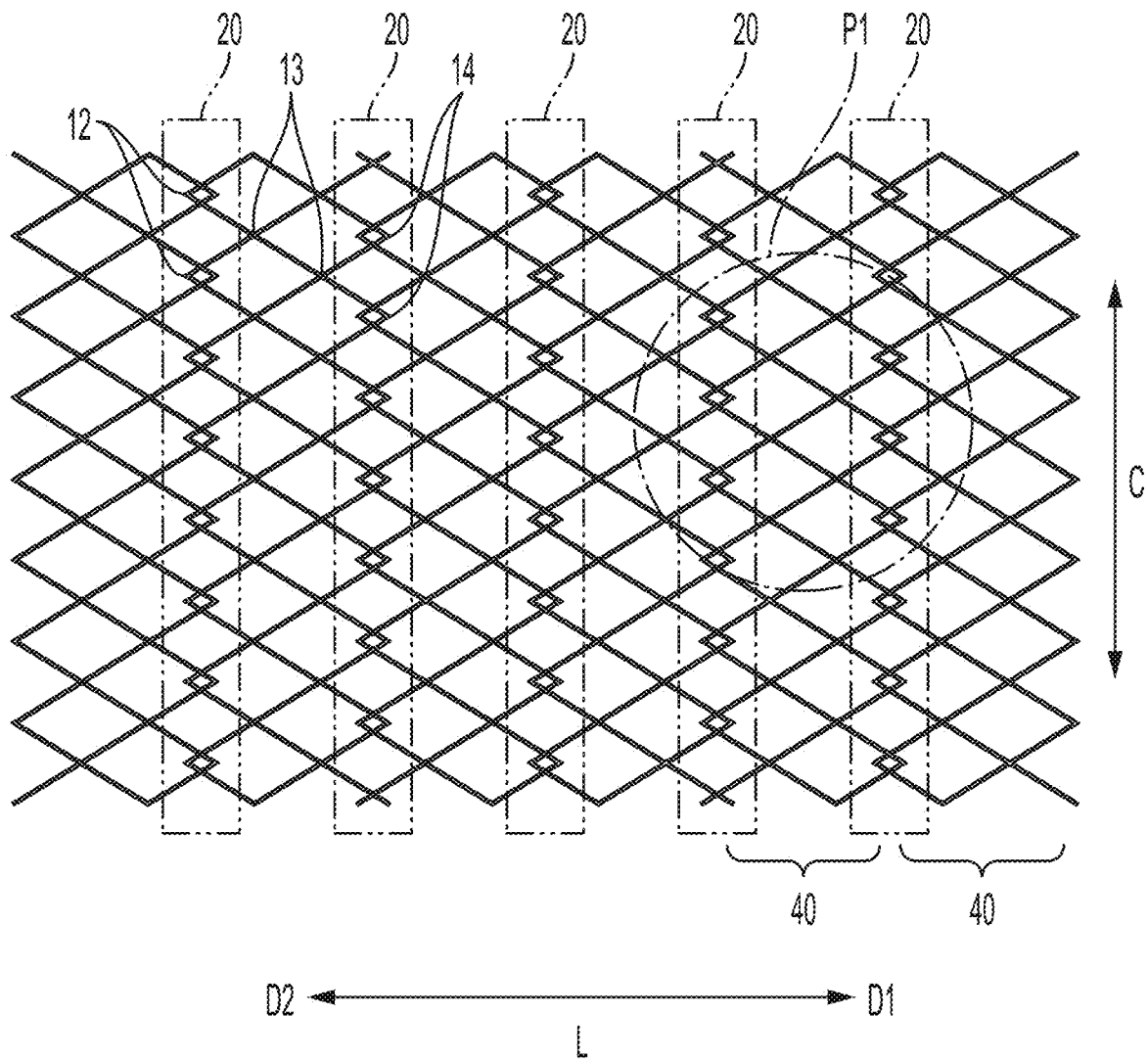
FIG. 4 is another view of a portion of the stent of FIG. 3 in which the circumferential surface is projected into a plane view.

FIG. 3 is a diagram schematically partially showing a configuration of a stent 100 according to an exemplary embodiment. FIG. 4 is a plane view of the stent 100 of FIG. 3 that is developed in a circumferential direction. The stent 100 in FIG. 3 is a self-expanded stent, which is be formed by weaving wires into a cylindrically shaped tubular fence. The stent 100 is usually placed in a lumen of a digestive system such as the bile duct, esophagus, duodenum, small intestine, and large intestine, and is mainly used for the purpose of expanding and retaining the lumen.

The stent 100 in this exemplary embodiment is an uncovered stent, meaning it is not coated with a film or the like as is found in a so-called covered stent, in which an outer peripheral surface side thereof is coated with a resin film or the like. However, the stent 100 can also be used as a covered stent by covering it with a resin film or the like.

As shown in FIGS. 3 and 4, the stent 100 may include a plurality of tubular units 40 and a plurality of connecting locations 20 that connect the plurality of tubular units 40 together to form a main body of the stent 100. The plurality of tubular units 40 are arranged around axially along a longitudinal center axis X (in FIG. 3) of the stent in a longitudinal center axis direction L (in FIG. 4). Any adjacent ones of the tubular units 40 are connected by the plurality of connecting locations 20.

In this exemplary embodiment, as will be described in detail below, the plurality of connecting locations 20 are also referred to as entangling connecting locations as each of the entangling connecting locations is formed by hooking two bent portions of the wires.

In the following description, one side of the axial direction L of the stent 100, which is the side of the distal end portion is also referred to as "first axial direction D1", and the other side of the axial direction L of the stent 100, which is the side of the proximal end portion is also referred to as "second axial direction D2".

Each of the tubular units 40 is formed in a circular shape, as part of the tubular fence, having meshes on its peripheral surface by means of extending wires in a circumferential direction C while repeatedly bending and crossing the wires.

Each of the tubular unit 40 includes a plurality of first bent portions 14 in which the wires bend in the first axial direction D1, a plurality of second bent portions 12 in which the wires bends in the second axial direction D2, and a plurality of intersecting portions 13 in which the wires cross each other, typically in a straight line.

In this exemplary embodiment, the plurality of first bent portions 14 are arranged along the circumferential direction C. Each of the first bent portions 14 is a convex portion in which the wire extending along the circumferential direction C is bent back in the longitudinal center axis direction L and becomes convex toward the first direction D1. On the other hand, the plurality of second bent portions 12 are arranged along the circumferential direction C. Each of the second bent portions 12 is a convex portion in which the wire extending along the circumferential direction C is bent back in the longitudinal center axis direction L and becomes convex toward the second direction D2.

Each of the connecting locations 20 is a portion in which adjacent ones of the tubular units 40 are connected in the longitudinal center axis direction L, and is formed by hooking the first bent portion 14 of the tubular unit 40 on the second direction D2 side to the second bent portion 12 of the tubular unit 40 on the first direction D1 side. Thus, the connecting locations 20 are also referred to as entangling connecting locations. Moreover, in each of the entangling connecting locations 20, the first bent portion 14 and the second bent portion 12 intersect in a "hook shape" in the radial direction and the longitudinal center axis direction, so that the adjacent ones of the tubular units 40 are connected in a state of being inseparable but relatively movable.

In the intersecting portion 13, the wires cross and overlap each other (in the radial direction), typically in straight lines, and at the point of crossing/overlapping, one wire is radially inward relative to the other wire. The intersecting portion 13 may be formed between adjacent ones of the entangling connecting locations 20 along the circumferential direction C, and/or may be formed between adjacent ones of the entangling connecting locations 20 in the longitudinal center axis direction L.

Figure 5:
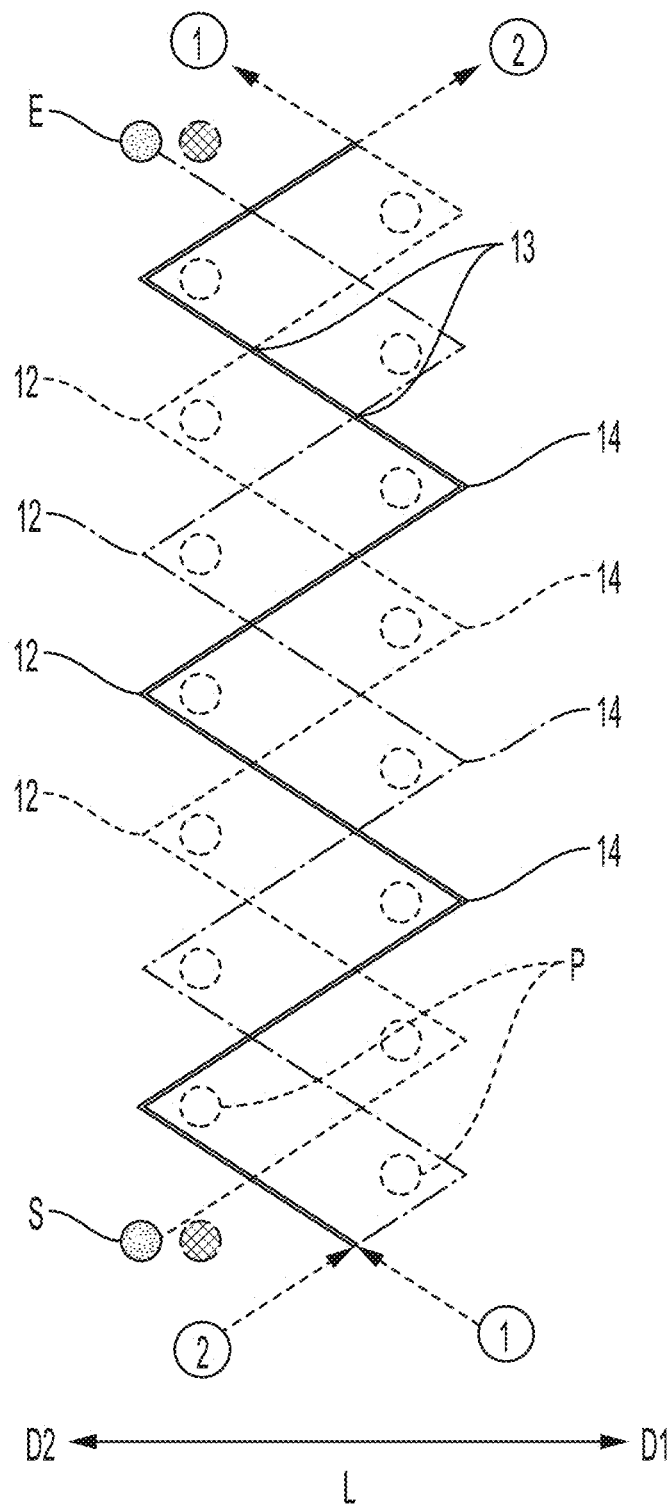
FIG. 5 shows an exemplary embodiment of a weaving pattern for a plurality of tubular units of a stent according to one exemplary embodiment.

FIG. 5 is a diagram showing an exemplary embodiment of how to weave the tubular units 40. The tubular units 40 are manufactured by using a manufacturing jig. The manufacturing jig may be formed of a cylindrical main body and a plurality of pins P erected on an outer peripheral surface of the main body. While not shown in FIG. 5, the plurality of pins P include first group pins and second group pins. Each of the first group pins includes a spacer 82, which will be described later in accordance with FIG. 10. Each of the second group pins does not have the spacer 82 and is in direct contact with the outer peripheral surface of the main body.

FIG. 5 is a view schematically illustrating the outer peripheral surface of the main body of the manufacturing jig, which is projected into a plane view. For explanation purposes, FIG. 5 only shows two rows of the pins P arranged around the circumferential direction C.

As shown in FIG. 5, the wire forming the tubular unit 40 extends inclined along the circumferential direction C from the start position S, and repeatedly forms the first bent portions 14 and the second bent portions 12. The wire makes a first round along the circumferential direction C and then makes a second round along the circumferential direction C (part ① shown in FIG. 5) and then makes a third round (part ② shown in FIG. 3) ending at finish position E.

The first round wire is represented by a dashed line in FIG. 5 extending from S at the bottom of FIG. 5 to part ① shown at the top of FIG. 5.

The second round wire is represented by a solid line in FIG. 5 extending from part ① at the bottom of FIG. 5 to part ② shown at the top of FIG. 5. The second round wire extends in an inclined direction along the circumferential direction C, and repeatedly forms the first bent portions 14 and the second bent portions 12. The first bent portion 14 formed by the wire on the second round is formed between the first bent portions 14 formed by the wire on the first round. The second bent portion 12 formed by the wire on the second round is formed between the second bent portions 12 formed by the wire on the first round. The second round wire forms a straight intersection 13 that intersects the first round wire.

The wire on the third circumference (represented by a one-dot dashed line in FIG. 5 extending from part ② at the bottom of FIG. 5 to point E) extends in an inclined direction along the circumferential direction C, and repeatedly forms the first bent portions 14 and the second bent portions 12. The first bent portion 14 formed by the wire on the third round is formed between the first bent portion 14 formed by the wire on the first round and the first bent portion 14 formed by the wire on the second round. The second bent portion 12 formed by the wire on the third round is formed between the second bent portion 12 formed by the wire on the first round and the second bent portion 12 formed by the wire on the second round.

The third round wire forms a straight intersection 13 that intersects the first round wire and the second round wire. The wire is woven to the end point E after making a third round along the circumferential direction C.

Ends of the wires located at the start position S and the end point E may be connected by using a joining method such as caulking, laser welding, brazing, or the like. In FIG. 5, the wire joins the ends of the second bent portion 12. However, considering that stress concentration is likely to occur at the ends, the wire may join at the straight part instead of the end parts of the first bent portion 14 and the second bent portion 12.

The wire may be a superelastic alloy whose main material is NiTi. The superelastic alloy containing NiTi as the main material is not permanently deformed at the time of weaving, and the woven shape is memorized by applying heat treatment in the woven state.

As shown in FIG. 5, the tubular unit 40 woven as described above constitutes two intersecting portions 13 on the line segment of the wire connecting the first bent portion 14 and the second bent portion 12. The tubular unit 40 of the invention is not limited to this configuration, and the intersecting portions 13 may be formed at any suitable location depending on the types or configurations of a stent.

Figure 6:
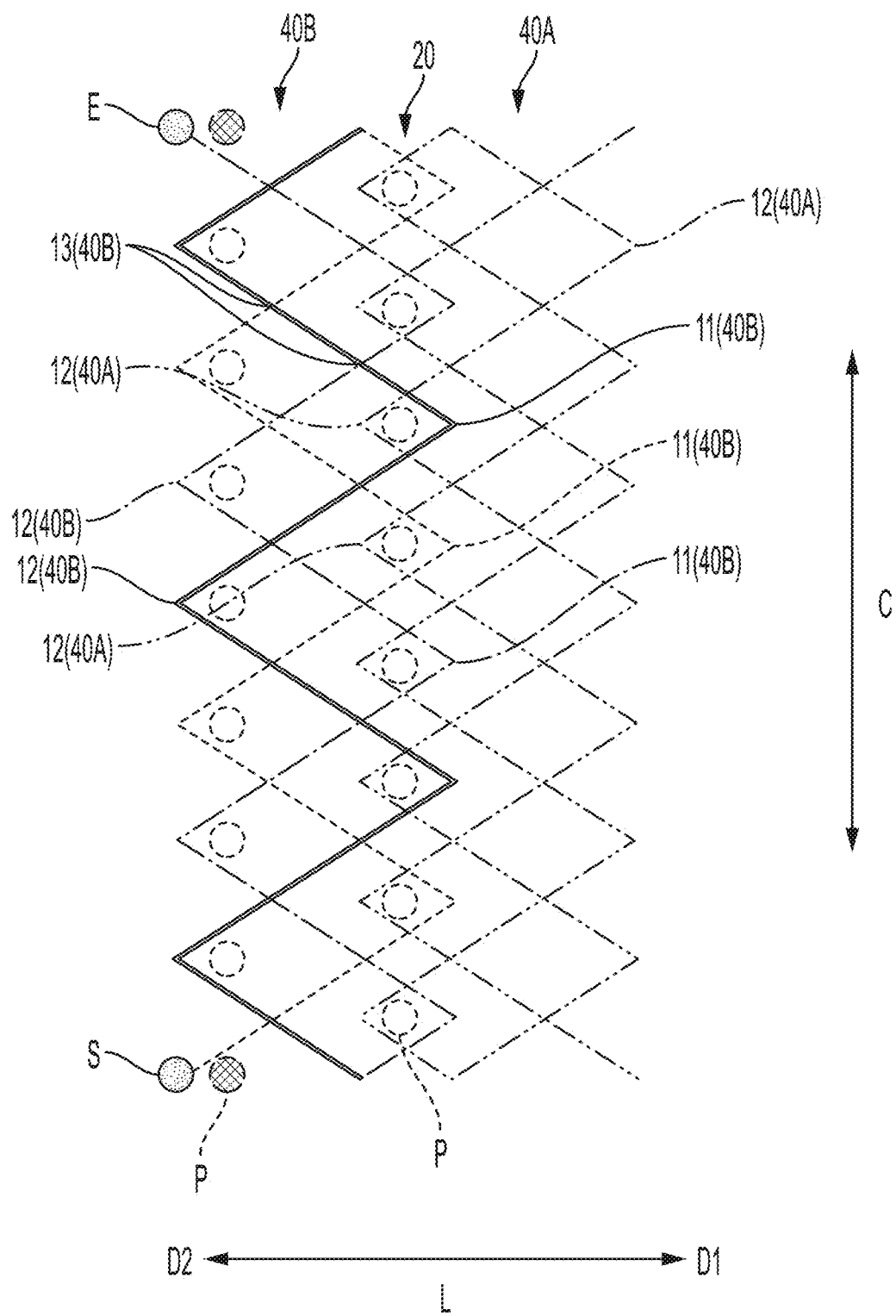
FIG. 6 shows an exemplary weaving pattern based on the pattern in FIG. 5, in which one tubular unit located on a first longitudinal direction side is connected to another tubular unit from a second longitudinal direction.

FIG. 6 shows an exemplary weaving method, in which one tubular unit 40 (hereinafter, "tubular unit 40A") located on the first direction D1 side is connected to the woven tubular unit 40 (hereinafter, referred to as "tubular unit 40B") from the second direction D2 side. As shown in FIG. 6, the tubular unit 40A is represented by a two-dot dashed line.

When the tubular unit 40B is manufactured using the manufacturing jig, a part of the pins used in manufacturing the tubular unit 40A is shared as shown in FIG. 6. Specifically, in FIG. 6, among the pins P arranged in two rows along the circumferential direction C, the pins P arranged in one row on the second direction D2 side are shared.

As shown in FIG. 6, the wire forming the tubular unit 40B extends obliquely along the circumferential direction C from the start position S, and repeatedly forms the first bent portions 14 and the second bent portions 12.

Figure 7:
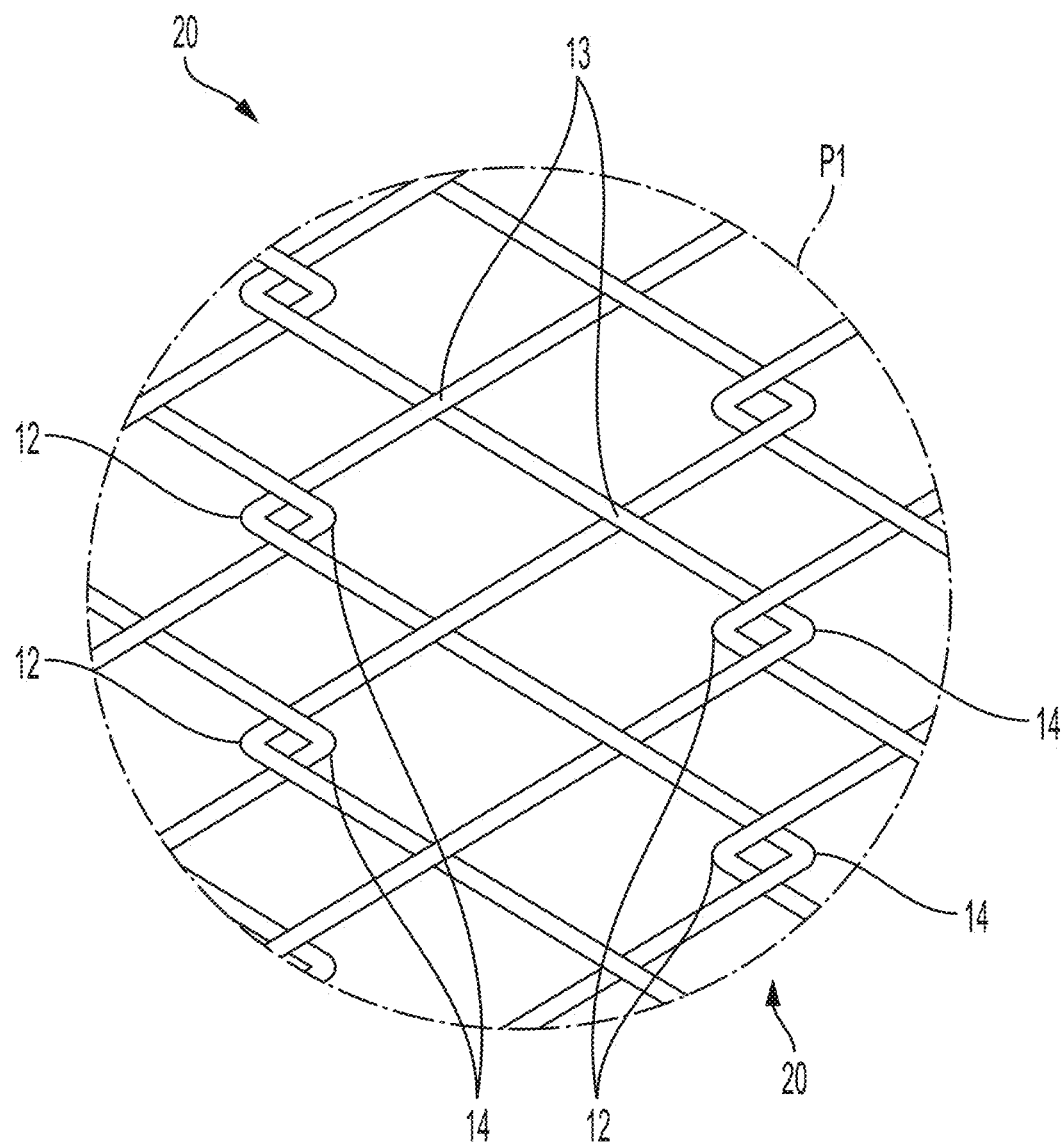
FIG. 7 is an enlarged view of an area P1 shown by a dashed line in FIG. 4.

FIG. 7 is an enlarged view of an area P1 shown by a dashed line in FIG. 4. When forming the first bent portion 14, the wire forming the tubular unit 40B intersects the second bent portion 12 of the tubular unit 40A in a "hook shape" in the radial and longitudinal directions to form the entangling portion 20.

Similar to the tubular unit 40A, the wire is woven up to the end point E after making a third round along the circumferential direction C. Both ends of the wires located at the start position S and the end point E are connected by using a joining method such as caulking, laser welding, brazing, or the like.

The tubular unit 40A and the tubular unit 40B are connected by the entangling connecting locations 20 so as to be relatively movable although they are inseparable. By this configuration, the tubular unit 40A and the tubular unit 40B can be connected without adding a new connecting member.

Each of the other tubular units 40 may be connected by the entangling connecting locations 20 in the same manner as the method in which the adjacent tubular units 40, the tubular unit 40A and the tubular unit 40B are connected by the entangling connecting locations 20. By connecting all the tubular units 40, the main body of the stent 100 is thus formed.

Figure 8A:
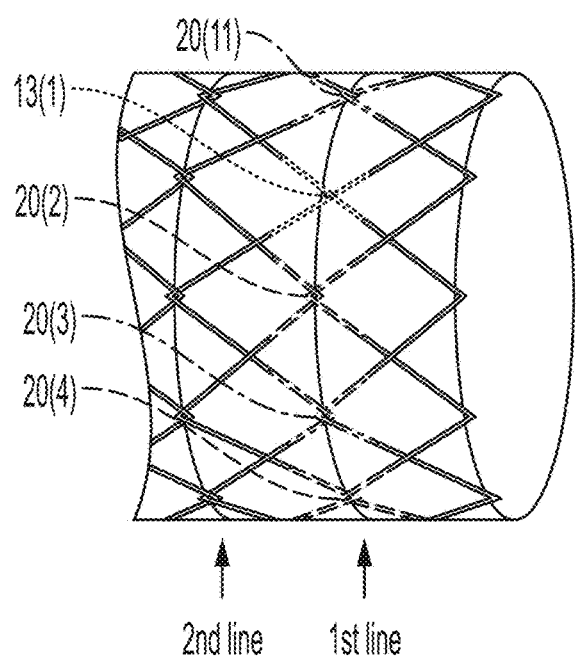
FIG. 8A is a perspective side view schematically illustrating part of the self-expanded stent, which is formed by weaving wires into a cylindrically shaped tubular fence according to one exemplary embodiment.

FIG. 8A is a perspective side view schematically illustrating part of the self-expanded stent 100, which is formed by weaving wires into a cylindrically shaped tubular fence according to one exemplary embodiment. The stent 100 includes a plurality of tubular units 40 connected by a plurality of entangling connecting locations 20 arranged along circumferential lines of the main body of the stent 100. As will be described in details below, these circumferential lines include circumferential lines such as 1st line and 2nd line in FIG. 8A that are arranged parallel with each other in the longitudinal center axis direction L, and also include circumferential lines C1-C4 in FIG. 14 that are concentric circles with respect to the longitudinal center axis X of the stent 100 and arranged parallel with each other in a radial direction of the stent 100.

Figure 8B:
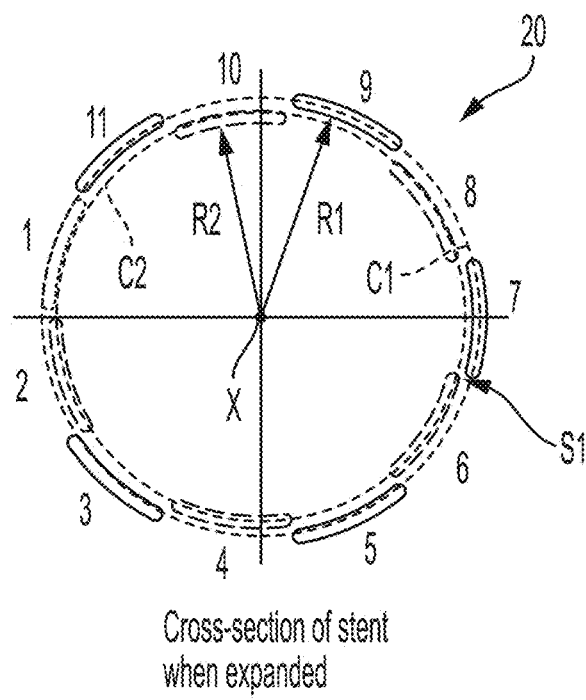
FIG. 8B is a front view (or cross-sectional view) schematically illustrating a structural arrangement of a plurality of circumferential sections of FIG. 8A.

For explanation purpose, FIG. 8A only shows two of such tubular units 40 which are connected by a plurality of entangling connecting locations 20. The difference between the stent 100 and the conventional stent is shown in FIG. 8B, but not in FIG. 8A. FIG. 8B is a front view (or cross-sectional view) schematically illustrating a structural arrangement of the plurality of entangling connecting locations 20 of FIG. 8A. In FIG. 8B, reference numeral 1 denotes an element representing one intersecting portion 13(1), which is formed between two adjacent ones of the entangling connecting locations 20. Reference numerals 2-11 denote ten elements representing the respective entangling connecting locations 20(2) to 20(11).

As shown in FIG. 8B, the plurality of entangling connecting locations 20(2)-20(11) are arranged along two concentric circumferential lines C1 and C2, the center of which is located on the longitudinal center axis X of the stent 100. There is a space between the circumferential lines C1 and C2 because the circumferential line C1 has a radius R1 that is greater than a radius R2 of the circumferential line C2. In this exemplary embodiment, the five entangling connecting locations 20(3), 20(5), 20(7), 20(9) and 20(11) are arranged along the circumferential line C1 and the five entangling connecting locations 20(2), 20(4), 20(6), 20(8) and 20(10) are arranged along the circumferential line C2. Any two adjacent entangling connecting locations 20 are respectively arranged along the respective circumferential lines C1 and C2. The intersecting portion 13 may be arranged either on the circumferential line C1 or the circumferential line C2.

The five entangling connecting locations 20(3), 20(5), 20(7), 20(9) and 20(11) do not overlap the five entangling connecting locations 20(2), 20(4), 20(6), 20(8) and 20(10) in a radial direction. Thus, a step S1 exists between any two adjacent ones of the entangling connecting locations 20(2)-20(11). The radius R1 is equal to a first distance between each of the entangling connecting locations 20(3), 20(5), 20(7), 20(9) and 20(11) and the longitudinal center axis X. The radius R2 is equal to a second distance between each of the entangling connecting locations 20(2), 20(4), 20(6), 20(8) and 20(10) and the longitudinal center axis X. As will be described later, the difference between the first and second distances or the difference between the radiuses R1 and R2 may be set to be a height H of the step S1 between the two adjacent entangling connecting locations 20 as shown in FIG. 10.

Figure 9:
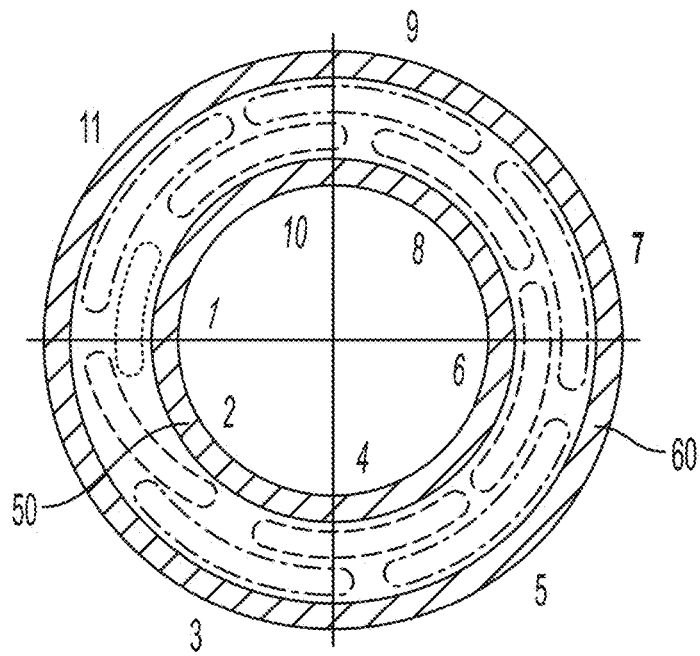
FIG. 9 is a front view (or cross-sectional view) schematically illustrating a stent when it is in a delivery configuration.

FIG. 9 is a front view (or cross-sectional view) schematically illustrating the stent 100 when it is in a delivery configuration. Since the stent 100 has to be delivered via the inner sheath 50 in an unexpanded diameter state, in which the diameter of the stent 100 is reduced by an external radial force so that the stent 100 can be compressed to be covered by the outer sheath 60 to a desired bodily location. Once at the desired bodily location, the outer sheath 60 is pulled back to expose the stent 100 such that the stent 100 can be self-expanded and implanted in a target area of the lumen. As shown in FIG. 9, during a delivery operation in which the stent 100 has to be stored between the inner sheath 50 and the outer sheath 60, the external radial force is required to push the entangling connecting locations 20 of the stent 100 so as to reduce the diameter of the stent 100. Since the step S1 is formed between any two adjacent entangling connecting locations 20, the any two adjacent entangling connecting locations 20 are pushed into the respective locations along the different circumferences. Thus, the any two adjacent entangling connecting locations 20 are prevented from pushing against each other, thereby avoiding a disorder arrangement of the entangling connecting locations 20. By this configuration, the stent 100 can be stored uniformly because the space between the inner sheath 50 and the outer sheath 60 can be utilized evenly and orderly no matter where the locations of the entangling connecting locations 20. As a result, this configuration can facilitate the operations of releasing and recapturing the stent 100 in the body.

Figure 10:
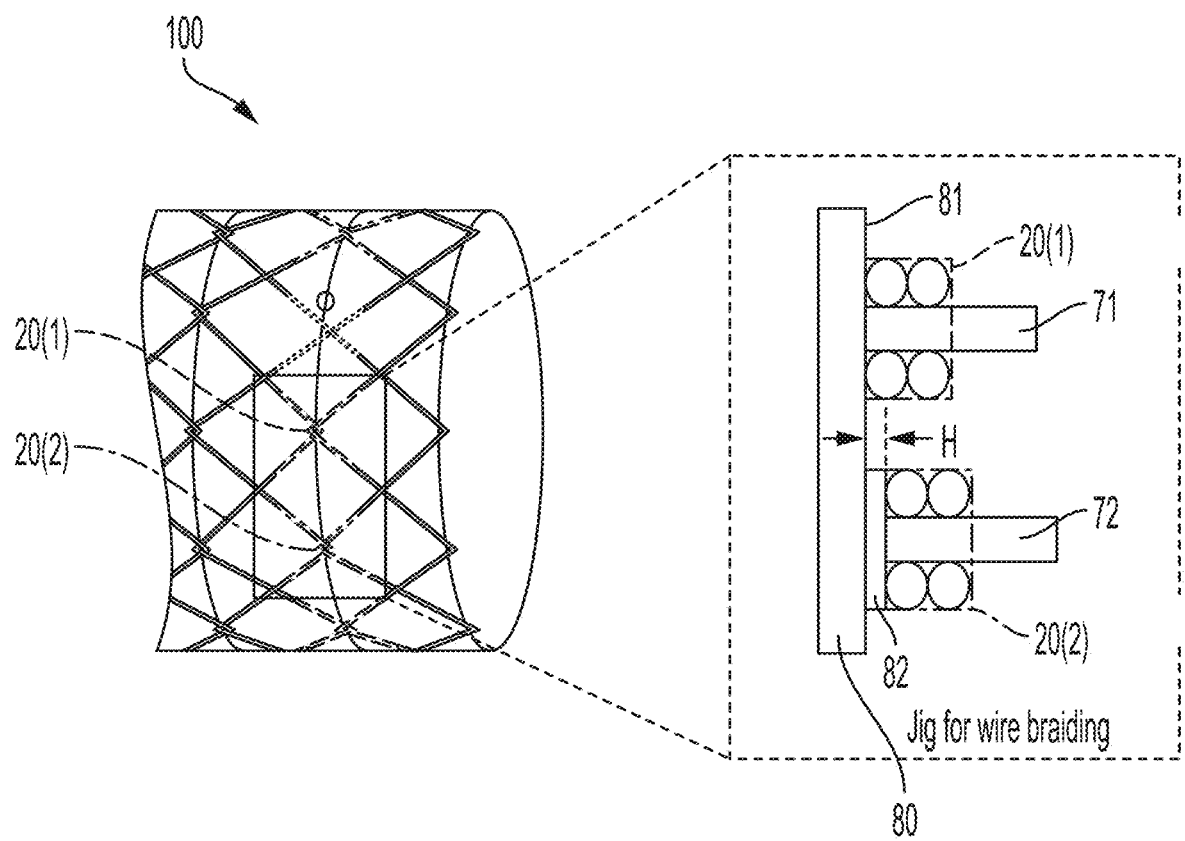
FIG. 10 is a diagram schematically illustrating an exemplary configuration in which a step, e.g., a change in radial distance, is formed between adjacent entangling portions of a stent according to one exemplary embodiment.

FIG. 10 is a diagram schematically illustrating an exemplary configuration in which a step formed between adjacent entangling connecting locations 20 of the stent 100 according to an exemplary embodiment. As described above, the stent 100 is formed by connecting the plurality of tubular units 40 in the longitudinal center axis direction L. As shown in FIG. 10, the stent 100 having the plurality of tubular units 40 can be manufactured by using a manufacturing jig, which includes a cylindrical main body 80 and the plurality of pins P erected on an outer peripheral surface 81 of the main body 80.

As shown in FIG. 10, the entangling connecting locations 20(1) and 20(2) are formed adjacent to each other along the circumferential direction C. The wires forming the entangling portion 20(1) are entangled around the pin 71, which is one of the second group pins, and the wires forming the entangling portion 20(2) are entangled around the pin 72, which is one of the first group pins. The entangling portion 20(1) is disposed in direct contact with the outer peripheral surface 81 of the main body 80, whereas the entangling portion 20(2) is disposed on the outer peripheral surface 81 via the spacer 82 so that the entangling portion 20(2) can be more radially outward than the entangling portion 20(1). In other words, the spacer 82 is disposed between the entangling portion 20(2) and the outer peripheral surface 81 of the main body 80. The spacer 82 is configured to generate the step S1 (in FIG. 8B) in a radial direction (or a radial offset) between the entangled connecting locations 20(1) and 20(2). The spacer 82 has a height H, which is set as a height of the step S1 formed between the entangling connecting locations 20(1) and 20(2).

In this exemplary embodiment, the height H of the step S1 is set to be at least equal to or greater than a radius of the wire used to make the stent 100. As shown in FIGS. 8B and 9, a step S1 formed between any adjacent ones of the entangling connecting locations 20 is configured to be able to provide a space, when the stent is in the delivery configuration, so that the entangling connecting locations 20(2), 20(4), 20(6), 20(8) and 20(10) can be compressed into locations along the circumference C2 that is closer to the inner sheath 50, whereas the respective adjacent entangling connecting locations 20(3), 20(5), 20(7), 20(9) and 20(11) can be compressed into locations along the circumference C1 that is closer to the outer sheath 60. Thus, the adjacent entangling portions are not pushed against each other when the stent 100 is stored between the inner sheath 50 and outer sheath 60 in the delivery (diameter reduced) configuration. By this configuration, the stent 100 can be stored orderly and uniformly between the inner sheath 50 and the outer sheath 60 in either the deliver operation or in the recapture operation.

Figures 11, 12:
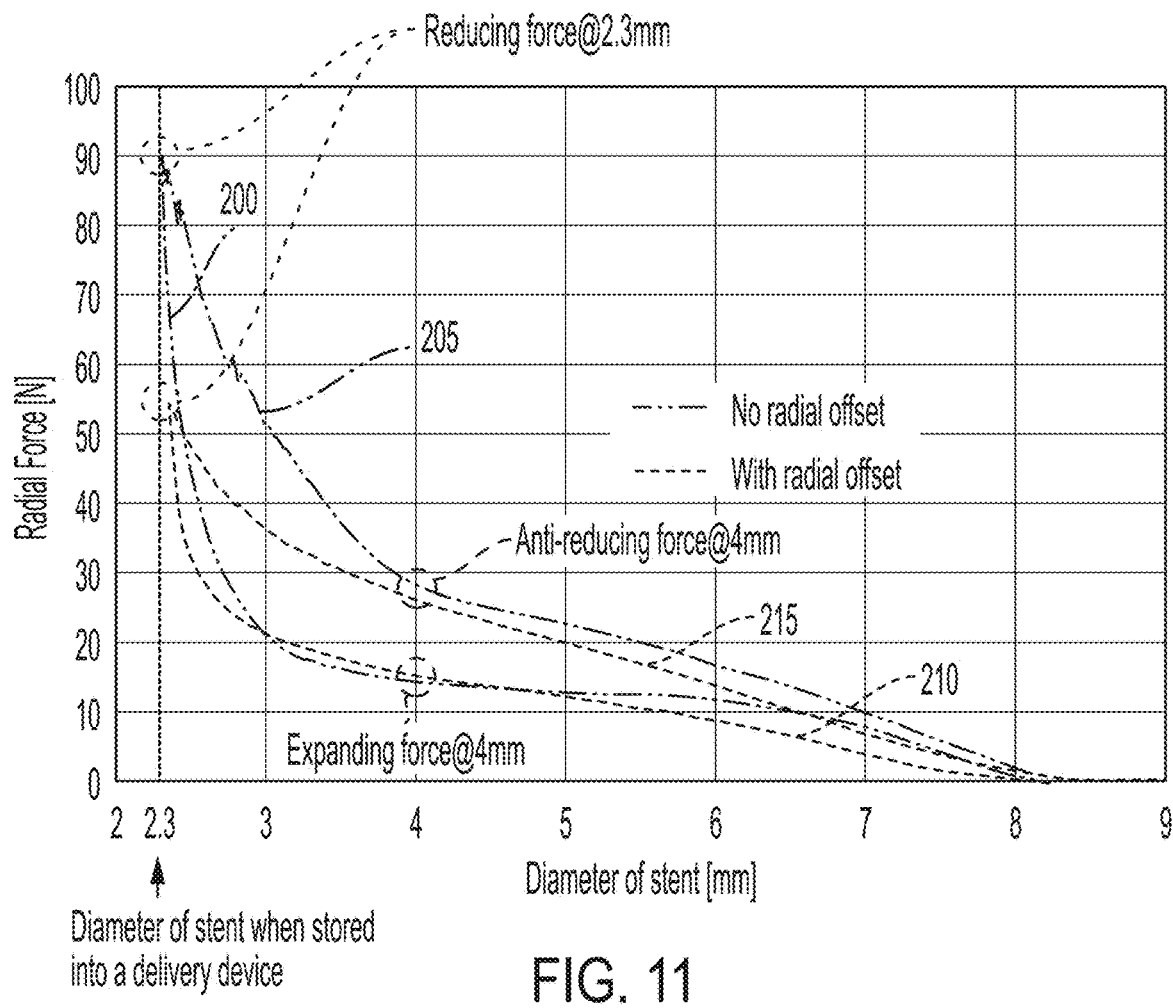
FIG. 11 is a graph showing radial force (N) as a function of diameter of stent (mm) for a conventional stent and a stent according to the exemplary embodiment.
FIG. 12 is a table illustrating the experimental results of the stent according to the exemplary embodiment.

FIG. 11 is a graph illustrating a relationship between a radial force and a diameter of a stent in comparison between the conventional stent and a stent according to the exemplary embodiment, and FIG. 12 is a table illustrating the experimental results of the stent according to the exemplary embodiment. In FIG. 11, line 200 represents a relationship between an expending radial force and the diameter of a conventional stent when the conventional stent is released, and line 205 represents a relationship between an anti-reducing radial force (a radial force against diameter reduction) and the diameter of the conventional stent when the conventional stent is stored between an inner sheath and an outer sheath of a delivery device. Line 210 represents a relationship between an expending radial force and the diameter of the stent 100, and line 215 represents a relationship between an anti-reducing radial force and the diameter of the stent 100.

As discussed above, since the conventional stent does not have the radial offset configuration in which at least one step formed between any adjacent ones of the entangling portions, a greater radial force is needed to release and recapture the conventional stent. Thus, as shown in FIGS. 11 and 12, when the conventional stent is stored in the delivery configuration, an anti-reducing radial force of 89.9 Newtons (N) is required to keep the conventional stent inside the delivery device. By contrast, an anti-reducing radial force of 54.8 (N) is needed to store the stent 100 between the inner sheath 50 and the outer sheath 60. The difference is 35.1 (N) or 39%.

On the other hand, when the conventional stent is in a release configuration in which the conventional stent self-expands into a target location, an expanding radial force of 89.9 (N) is required to fully expand the conventional stent. By contrast, the stent 100 just needs an expending radial force of 54.8 (N) to fully expand into the target location. The difference is 35.1 (N) or 39%. With the radial offset configuration, it is easy to release and recapture the stent 100.

As described above, in the radial offset configuration of the stent 100, one step is formed in a radial direction between any adjacent ones of the entangling portions arranged along the circumferential direction C. Also, the step may be formed in a radial direction between any adjacent ones of the entangling portions in the longitudinal center axis direction L. Moreover, the invention is not limited to the above configurations, and the stent 100 may have multiple-step configuration among the entangling portions either along the circumferential direction C and/or in the longitudinal direction L.

Figure 13:
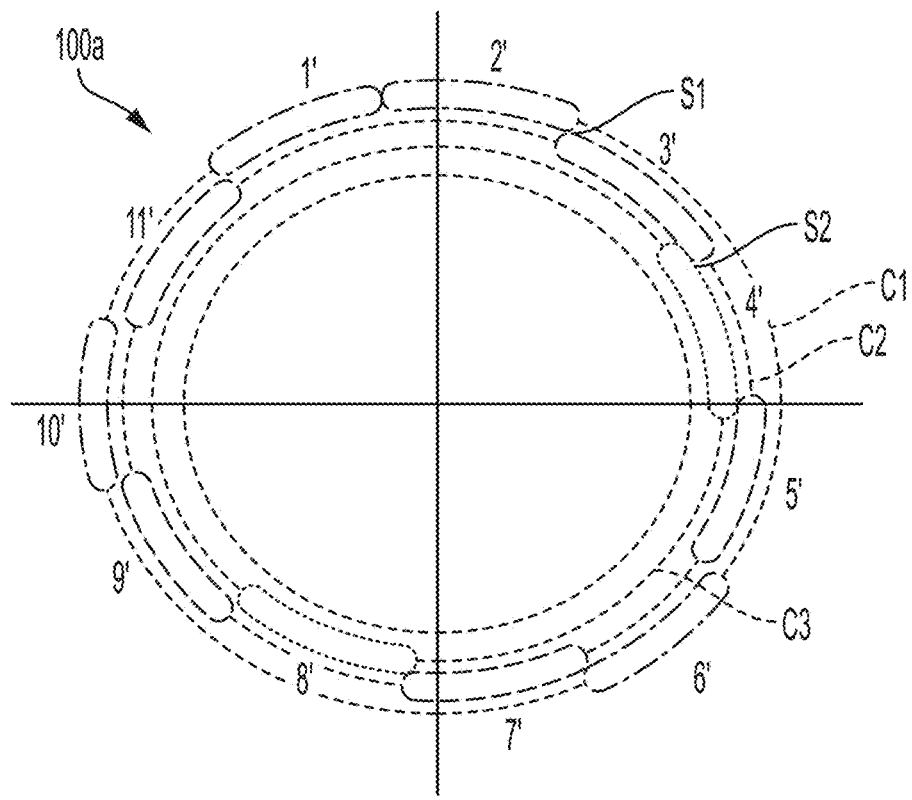
FIG. 13 is a front view schematically illustrating a stent including a two-step configuration according to one exemplary embodiment.
Figure 14:
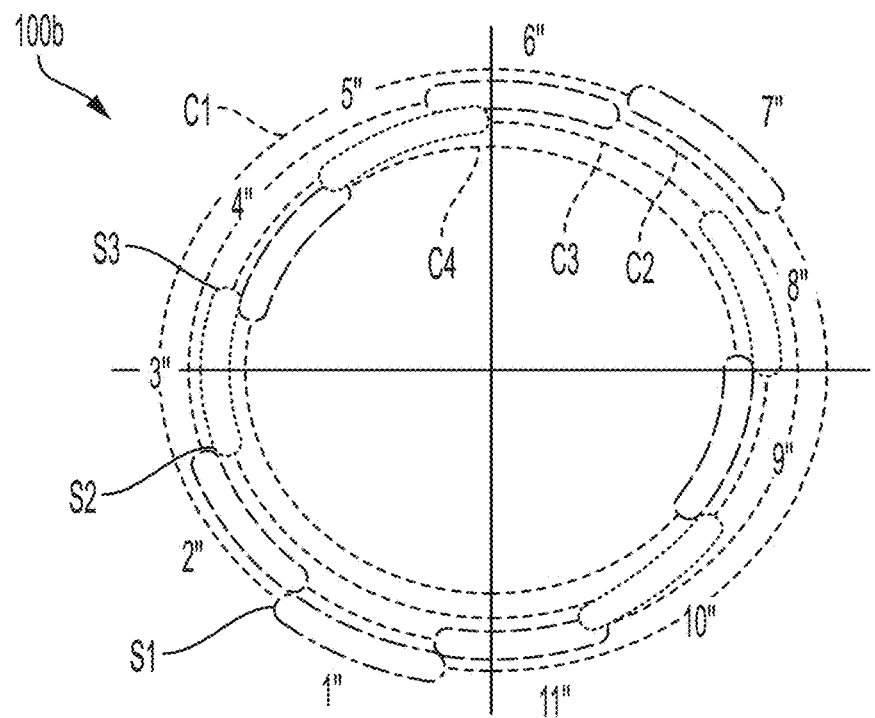
FIG. 14 is a front view schematically illustrating a stent including a three-step configuration according to one exemplary embodiment.
Figures 15A, 15B, 15C, 15D, 15E:
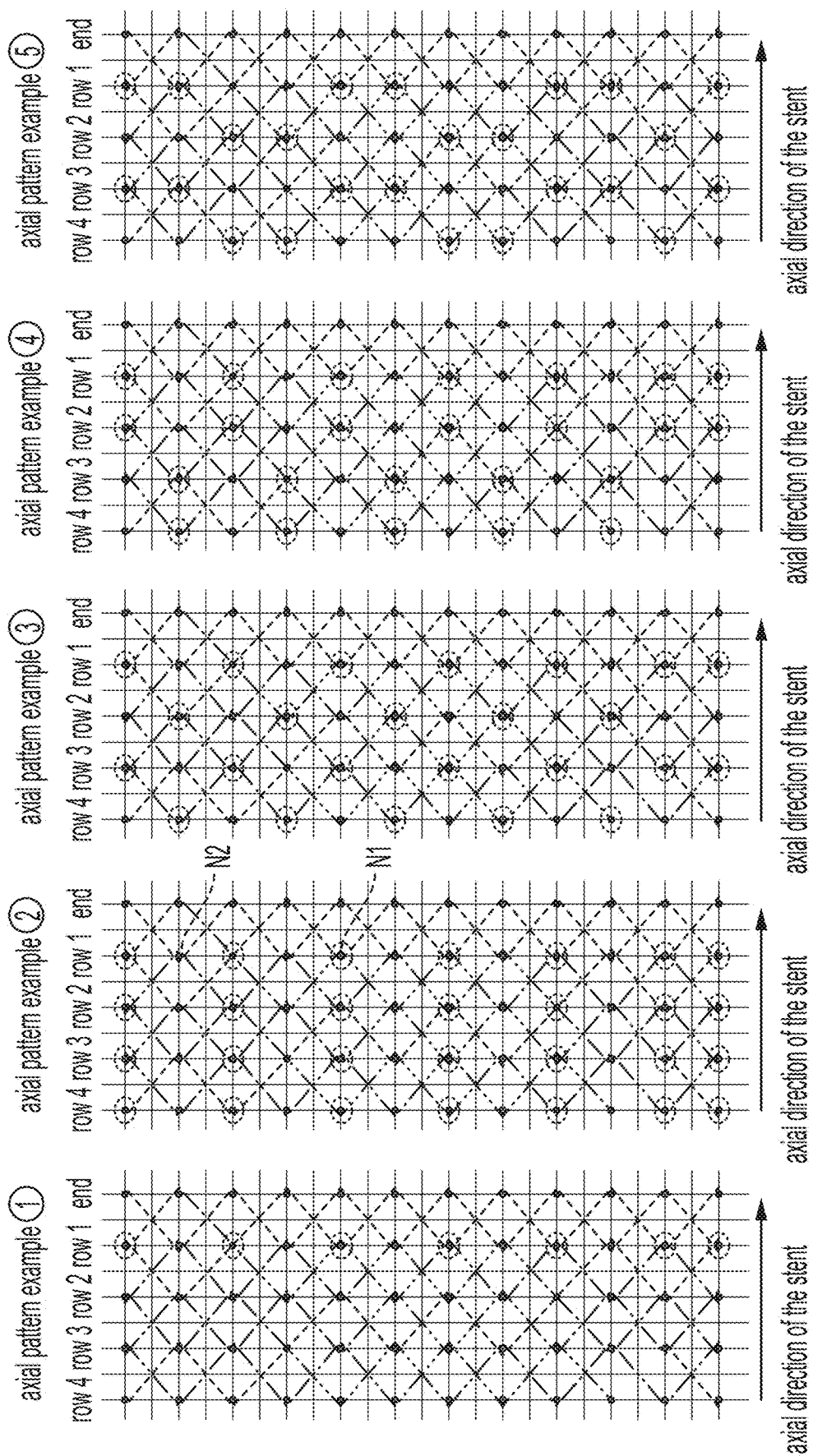
FIGS. 15A to 15E are diagrams schematically illustrating exemplary patterns of steps existing between the entangling portions of a stent in both the circumferential direction and the longitudinal center axis direction according to one exemplary embodiment.

FIG. 13 is a front view schematically illustrating a stent 100*a* including a two-step configuration according to one exemplary embodiment, and FIG. 14 is a front view schematically illustrating a stent 100*b* including a three-step configuration according to one exemplary embodiment.

In the exemplary embodiment shown in FIG. 13, the stent 100*a* is the same as the stent 100 as described above except that the stent 100*a* includes an intersecting portion 1' and a plurality of entangling portions 2'-11' that are arranged along at least three circumferences C1-C3. The three circumferences C1-C3 are concentric circles with different radiuses. In this exemplary embodiment, the intersecting portion 1' and three entangling portions 2', 6' and 10' are arranged along the circumference C1; five entangling portions 3', 5', 7', 9' and 11' are arranged along the circumference C2; and two entangling portions 4' and 8' are arranged along the circumference C3.

As shown in FIG. 13, the multi-step configuration of the stent 101*a* includes at least two steps S1 and S2 respectively formed between two entangling portions that are adjacent to each other but arranged along the different circumferences C1 to C3. Since the circumferences C1 to C3 are the concentric circles with the different radiuses, the two steps S1 and S2 are each formed by arranging any adjacent ones of the entangling portions along the different circumferences so as to generate the radial offset. For example, the step S1 between the adjacent entangling portions 2' and 3' is formed by arranging them along the respective circumferences C1 and C2 such that the entangling portion 2' is positioned radially outward with respect to the entangling portion 3'. Also, a step S2 between the adjacent entangling portions 3' and 4' is formed by arranging them along the respective circumferences C2 and C3 such that the entangling portion 3' is positioned radially outward with respect to the entangling portion 4'.

The intersecting portion 1' is arranged on the circumferential line C1, but it may also be arranged along the circumferential line C2 or C3.

In the exemplary embodiment shown in FIG. 14, the stent 100*b* is the same as the stent 100 as described above except that the stent 100*b* includes a plurality of entangling portions 1"-11" that are arranged along at least four circumferences C1-C4. The four circumferences C1-C4 are concentric circles and have different radius. In this exemplary embodiment, the two entangling portions 1" and 7" are arranged along the circumference C1; the three entangling portions 2", 6" and 11" are arranged along the circumference C2; the four entangling portions 3", 5", 8" and 10" are arranged along the circumference C3, and the two entangling portions 4" and 9" are arranged along the circumference C4.

As shown in FIG. 14, the multi-step configuration of the stent 100*b* includes at least three steps S1 to S3 formed between any two of the entangling portions 1"-11" that are adjacent to each other but arranged along the respective two of the different circumferences C1-C4. Since the circumferences C1 to C4 are the concentric circles with the different radiuses, the three steps S1 to S3 are each formed by arranging any adjacent ones of the entangling portions along the different circumferences so as to generate the radial offset. For example, the step S1 between the adjacent entangling portions 1" and 2" is formed by arranging them along the respective circumferences C1 and C2 such that the entangling portion 1' is positioned radially outward with respect to the entangling portion 2". The step S2 between the adjacent entangling portions 2" and 3" is formed by arranging them along the respective circumferences C2 and C3 such that the entangling portion 2" is positioned radially outward with respect to the entangling portion 3". Also, the step S3 between the adjacent entangling portions 3" and 4" is formed by arranging them along the respective circumferences C3 and C4 such that the entangling portion 3" is positioned radially outward with respect to the entangling portion 4".

FIGS. 15A to 15E are diagrams schematically illustrating exemplary patterns in which the steps exist between the entangled connecting portions of the stent in both the circumferential direction and the longitudinal center axis direction according to one exemplary embodiment. Each of FIGS. 15A to 15E illustrates a tubular stent cut in a longitudinal axial direction (arrow direction) and unfolded as a plan view.

The dashed lines are the wires that make up the stent. The dots N1 are each an entangled connecting node where the wires that make up the stent are entwined. When the stent is in a tubular state or in a fully self-expanded state, a distance between the longitudinal central axis of the stent and the dot N1 is longer than a distance between the longitudinal central axis and a dot N2.

FIGS. 15A to 15E show the various exemplary arrangement patterns of the dots N1 (entwined notes). When the tubular stent is placed in a lumen of the body, the tubular stent may be unexpectedly contracted. In this situation, the function of securing the space of the lumen, which is the purpose of the stent, is impaired. Thus, it is important to change the number of the dots N1 and the arrangement patterns according to the material of the stent and the nature of the lumen, so that the ease of the contraction of the tubular stent can be appropriately adjusted, thereby avoiding the unexpected contraction.

With the above described configurations, the stent 100, 100*a* or 100*b* may be stored in a delivery system in a reduced diameter state and is transported to the affected area where stenosis or occlusion has occurred. The stent 100, 100*a* or 100*b* released from the delivery system expand its diameter by self-expansion to expand stenosis and occlusion. Since the stent 100, 100*a* or 100*b* has the above-described structural configurations, the delivery operation as well as the recapture operation of the stent 100, 100a or 100b become easy.

The stents 100, 100a and 100b may be made from any suitable implantable material, including without limitation nitinol, stainless steel, cobalt-based alloy such as Elgiloy®, platinum, gold, titanium, tantalum, niobium, polymeric materials and combinations thereof Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly (L-lactide-co-glycolide) (PLLA/PGA), poly(D,L-lactide-co-glycolide) (PLA/PGA), poly(glycolide-co-trimethylene carbonate) (PGAlPTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGAlPCL), poly (phosphate ester) and the like.

Further, the stents 100, 100a and 100b, or portions thereof, may have a composite construction. For example, the stents 100, 100a and 100b may have an inner core of tantalum gold, platinum, iridium or combination of thereof and an outer member or layer of nitinol to provide a composite wire for improved radiocapicity or visibility. Or the stents 100, 100a and 100b may be made from nitinol.

Also, the stents 100, 100a and 100b may be treated with any known or useful bioactive agent or drug including without limitation the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hiradin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anticoagulants (such as D-Phe-Pro-Arg chloromethyl keton, an ROD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors twin as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasco-active mechanisms.

The stents 100, 100a and 100b may be coated with a polymeric material. For example, the stent wires of the stent 30 may be partially or fully covered with a biologically active material which is equitably disposed with the polymeric material. Further, the polymeric coating may extend over or through the interstitial spaces between the stent wires so as to provide a hollow tubular liner or cover over the interior or the exterior surface of the stent, thereby providing a stent-graft device. The polymeric material may be selected from the group consisting of polyester, polypropylene, polyethylene, polyurethane, polynaphthalene, polytetrafluoroethylene, expanded polytetrafluoroethylene, silicone, and combinations thereof. The covering may be in the form of a tubular structure. The silicone covering may be suitably formed by dip coating the stent. The present invention is not limited to forming the silicone film by dip coating, and other techniques, such as spraying, may suitably be used. After applying the silicone coating or film to the stent, the silicone may be cured. The curing may be low temperature curing, for example from about room temperature to about 90° C. for a short period of time, for example from about 10 minutes or more to about 16 hours. The cured silicone covering may also be sterilized by electronic beam radiation, gamma radiation ethylene oxide treatment and the like. Argon plasma treatment of the cured silicone may also be used. Argon plasma treatment of the cured silicone modifies the surface to the cured silicone to, among other things, make the surface less sticky. The invention, however, is not limited to stent-graft devices having polymeric coatings. The graft portion may suitably be formed from polymeric films, polymeric tapes, polymeric tubes, polymeric sheets and textile materials. Textile material may be woven and/or filament wound to provide a suitable graft.

Various biocompatible polymeric materials may be used as textile materials to form the textile structures, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. Moreover, textile materials and stent materials may be co-formed, for example co-woven, to form a stent-graft device.

Various self-expanding stents may be employed in the invention. The self-expanding stents may include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents, including biodegradable and bioabsorbable stents. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

The inner sheath 50 and/or the outer sheath 60 may be constructed of any suitable biocompatible materials, such as, but not limited to, polymeric polymers and materials, including fillers such as metals, carbon fibers, glass fibers or ceramics, and combinations thereof. Useful, but non-limiting, polymeric materials include polyethylene, polypropylene, polyvinyl chloride, polytetrafluoroethylene, fluorinated ethylene propylene copolymer, polyvinyl acetate, polystyrene, polyethylene terephthalate), naphthalene dicarboxylate derivatives, such as polyethylene naphthalate, polybutylene naphthalate, polytrimethyiene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, fully or partially halogenated polyethers, polyamidelpolyether polyesters, and copolymers and combinations thereof.

Further, the inner sheath 50 and/or the outer sheath 60 may be reinforced to provide greater strength while minimizing overall tube profile. For example, the inner sheath 50 and/or the outer sheath 60 may have a reinforcing material, for example a polymeric, metallic or ceramic strand or tape, encased within the tube or otherwise disposed on or within the tube. The reinforcing strand or tape may be woven, woven, wound, and the life to form a reinforcing member for the tube.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

What is claimed is:

1. A stent, comprising:
   a wire that is woven into a tubular fence forming a stent body;
   a plurality of tubular units connected around a longitudinal center axis of the stent body; and
   a plurality of connecting locations configured to connect adjacent ones of the plurality of tubular units and arranged along a plurality of circumferences with respect to the longitudinal center axis of the stent body,
   wherein the plurality of circumferences include a first circumference having a first radius and a second circumference having a second radius, and the first radius is different from the second radius in length,
   wherein the plurality of connecting locations include first connecting locations arranged along the first circumference, and second connecting locations arranged along the second circumference, and
   wherein each of the first connecting locations is located at the first radius and each of the second connecting locations is located at the second radius.

2. The stent according to claim 1, wherein a difference in the first radius and the second radius forms a step between the each of the first connecting locations and each of the second connecting locations, and wherein the step has a height that is at least equal to a radius of the wire of the stent.

3. The stent according to claim 1, wherein the first circumference and the second circumference are concentric circles.

4. The stent according to claim 1, wherein the first circumference is spaced-apart from the second circumference along the longitudinal center axis of the stent.

5. A stent, comprising:
   a wire that is woven into a tubular fence forming a stent body;
   a plurality of tubular units connected around a longitudinal center axis of the stent body; and
   a plurality of connecting locations configured to connect adjacent ones of the plurality of tubular units and arranged along a plurality of circumferences with respect to the longitudinal center axis of the stent body,
   wherein the plurality of circumferences include a first circumference having a first radius and a second circumference having a second radius, and the first radius is different from the second radius in length,
   wherein the plurality of circumferences further include a third circumference having a third radius that is different from the first and second radiuses in length,
   wherein the plurality of connecting locations further include third connecting locations arranged along the third circumference, and
   wherein each of the first connecting locations is located at the first radius, each of the second connecting portions is located at the second radius, and each of the third connecting portions is located at the third radius.

6. The stent according to claim 5, wherein a difference in the first radius and the second radius forms a first step between the each of the first connecting locations and each of the second connecting locations, and a difference in the second radius and the third radius forms a second step between the each of the second connecting locations and each of the third connecting locations, and
   wherein the first and second steps each have a height that is no less than a radius of the wire of the stent.

7. The stent according to claim 5, wherein the first, second and third circumferences are concentric circles.

8. The stent according to claim 5, wherein the plurality of circumferences further include a fourth circumference having a fourth radius that is different from the first, second and third radiuses in length,
- wherein the plurality of connecting locations further include fourth connecting locations arranged along the fourth circumference, and
- wherein each of the fourth connecting portions is located at the fourth radius.

9. The stent according to claim 8, wherein a difference in the third radius and the fourth radius forms a third step between the each of the third connecting locations and each of the fourth connecting locations, and the first, second, third and fourth steps each have a height that is no less than a radius of the wire of the stent.

10. The stent according to claim 8, wherein the fourth circumference is a concentric circle with the first, second and third circumferences.

11. A stent, comprising:
- a wire that is woven into a tubular fence forming a stent body;
- a plurality of tubular units connected around a longitudinal center axis of the stent body; and
- a plurality of connecting locations configured to connect adjacent ones of the plurality of tubular units and arranged along a plurality of circumferences with respect to the longitudinal center axis of the stent body,
- wherein the plurality of circumferences include a first circumference having a first radius and a second circumference having a second radius, and the first radius is different from the second radius in length,
- wherein each of the plurality of the connecting locations is formed by hooking a first bent portion of the wire and a second bent portion of the wire, and
- wherein the first bent portion is a first convex portion in which the wire extending along a circumferential direction is bent back toward one side of a longitudinal center axis direction, and the second bent portion is a second convex portion in which the wire extending along the circumferential direction is bent back toward an opposite side of the longitudinal center axis direction.

12. A stent, comprising:
- a wire that is woven into a tubular fence;
- a first entangled connecting portion that is formed by hooking a first bent portion and a second bent portion of the wire; and
- a second entangled connecting portion that is formed by hooking a third bent portion and a fourth bent portion of the wire,
- wherein the first bent portion is adjacent to the third bent portion along a circumferential direction, and the second bent portion is adjacent to the fourth bent portion along the circumferential direction, and
- wherein a first radial distance between the first entangled connecting portion and a longitudinal center axis of the stent is different from a second radial distance between the second entangled connecting portion and the longitudinal center axis of the stent.

13. The stent according to claim 12, wherein the first bent portion is a first convex portion in which the wire extending along the circumferential direction is bent back toward one side of a longitudinal center axis direction, and the second bent portions is a second convex portion in which the wire extending along the circumferential direction is bent back toward an opposite side of the longitudinal center axis direction.

14. The stent according to claim 13, wherein a difference between the first radial distance and the second radial distance is a height of a step formed between the first entangling portion and the second entangling portion.

15. The stent according to claim 14, wherein the height of the step is at least equal to a radius of the wire.

16. The stent according to claim 12, wherein the first entangled connecting portion is arranged along a first circumference and the second entangled connecting portion is arranged along a second circumference, and
- wherein the first and second circumference are concentric circles.

17. The stent according to claim 12, wherein the first entangled connecting portion is arranged along a first circumference and the second entangled connecting portion is arranged along a second circumference, and
- wherein the first circumference is adjacent to the second circumference along a longitudinal center axis of the stent.

18. The stent according to claim 12, further comprising a third entangled connecting portion, and
- wherein a third radial distance between the third entangled connecting portion and the longitudinal center axis of the stent is different from the first radial distance and the second radial distance.

* * * * *